United States Patent
Smith

(10) Patent No.: US 7,918,827 B2
(45) Date of Patent: Apr. 5, 2011

(54) SEAL ASSEMBLY FOR SURGICAL ACCESS DEVICE

(75) Inventor: Robert C. Smith, Middletown, CT (US)

(73) Assignee: Tyco Healthcare Group LP, New Haven, CT (US)

(*) Notice: Subject to any disclaimer, the term of this patent is extended or adjusted under 35 U.S.C. 154(b) by 0 days.

(21) Appl. No.: 11/903,853

(22) Filed: Sep. 25, 2007

(65) Prior Publication Data

US 2009/0082720 A1    Mar. 26, 2009

(51) Int. Cl.
*A61M 5/178* (2006.01)
*A61M 5/14* (2006.01)
*A61B 17/32* (2006.01)

(52) U.S. Cl. .............. 604/167.06; 604/256; 604/30; 606/167

(58) Field of Classification Search .......... 604/246, 604/103.03, 256, 278, 30
See application file for complete search history.

(56) References Cited

U.S. PATENT DOCUMENTS

| | | |
|---|---|---|
| 4,007,909 A | 2/1977 | Buseth et al. |
| 4,126,133 A | 11/1978 | Schwartz |
| 4,473,211 A | 9/1984 | Fremy |
| 4,586,694 A | 5/1986 | Jones |
| 4,655,752 A | 4/1987 | Honkanen et al. |
| 4,686,977 A | 8/1987 | Cosma |
| 4,874,378 A | 10/1989 | Hillstead |
| 4,917,668 A | 4/1990 | Haindl |
| 4,929,235 A | 5/1990 | Merry et al. |
| 4,960,412 A | 10/1990 | Fink |
| 5,123,634 A | 6/1992 | Schwerdt |
| 5,127,626 A | 7/1992 | Hilal et al. |
| 5,197,955 A | 3/1993 | Stephens et al. |
| 5,201,714 A | 4/1993 | Gentelia et al. |
| 5,209,736 A | 5/1993 | Stephens et al. |
| 5,209,737 A | 5/1993 | Ritchart et al. |
| 5,211,633 A | 5/1993 | Stouder, Jr. |
| 5,221,264 A | 6/1993 | Wilk et al. |
| 5,224,930 A | 7/1993 | Spaeth et al. |
| 5,242,412 A | 9/1993 | Blake, III |

(Continued)

FOREIGN PATENT DOCUMENTS

EP    0 538 060    9/1995

(Continued)

OTHER PUBLICATIONS

European Search Report for corresponding EP 082513100, date of mailing is Dec. 12, 2008 (3 pages).

*Primary Examiner* — Kevin C Sirmons
*Assistant Examiner* — Imani Hayman

(57) ABSTRACT

Seal assemblies are provided, comprising a seal holder including a cylindrical wall portion having a tapered distal portion, wherein the cylindrical wall portion defines a central passage. The seal assembly comprises a ball seal supported in the central passage of the seal holder. The ball seal includes a distal aperture and a proximal aperture, wherein the distal and/or proximal aperture is dimensioned for substantial sealed reception with a surgical instrument. The ball seal is adapted for angular movement relative to a central longitudinal axis of the seal holder upon angulation of the surgical instrument, whereby the ball seal substantially maintains the seal with the surgical instrument. The seal assembly comprises a seal cover defining an aperture formed in a transverse wall thereof. The seal cover is configured for connection with the seal holder for maintaining the ball seal within the central passage of the seal holder.

23 Claims, 15 Drawing Sheets

U.S. PATENT DOCUMENTS

| | | |
|---|---|---|
| 5,251,873 A | 10/1993 | Atkinson et al. |
| 5,273,545 A | 12/1993 | Hunt et al. |
| 5,295,657 A | 3/1994 | Atkinson |
| 5,300,033 A | 4/1994 | Miller |
| 5,300,035 A | 4/1994 | Clement |
| 5,308,336 A | 5/1994 | Hart et al. |
| 5,330,436 A | 7/1994 | Heidmueller |
| 5,338,307 A | 8/1994 | Stephens et al. |
| 5,350,362 A | 9/1994 | Stouder, Jr. |
| 5,366,446 A | 11/1994 | Tal et al. |
| 5,380,288 A | 1/1995 | Hart et al. |
| 5,385,553 A | 1/1995 | Hart et al. |
| 5,389,080 A | 2/1995 | Yoon |
| 5,389,081 A | 2/1995 | Castro |
| 5,391,153 A | 2/1995 | Haber et al. |
| 5,395,342 A | 3/1995 | Yoon |
| 5,397,335 A | 3/1995 | Gresl et al. |
| 5,403,284 A | 4/1995 | Gross |
| 5,405,330 A | 4/1995 | Zunitch et al. |
| 5,407,433 A | 4/1995 | Loomas |
| 5,411,483 A | 5/1995 | Loomas et al. |
| 5,423,761 A | 6/1995 | Hein et al. |
| 5,429,609 A | 7/1995 | Yoon |
| 5,441,486 A | 8/1995 | Yoon |
| 5,460,616 A | 10/1995 | Weinstein et al. |
| 5,476,475 A | 12/1995 | Gadberry |
| 5,478,318 A | 12/1995 | Yoon |
| 5,492,304 A | 2/1996 | Smith et al. |
| 5,496,280 A | 3/1996 | Vandenbroek et al. |
| 5,509,643 A | 4/1996 | Carstens et al. |
| 5,512,053 A | 4/1996 | Pearson et al. |
| 5,514,133 A | 5/1996 | Golub et al. |
| 5,531,758 A | 7/1996 | Uschold et al. |
| 5,540,661 A | 7/1996 | Tomisaka et al. |
| 5,545,142 A | 8/1996 | Stephens et al. |
| 5,554,124 A | 9/1996 | Alvarado |
| 5,569,205 A | 10/1996 | Hart et al. |
| 5,584,847 A | 12/1996 | Duluco et al. |
| 5,584,850 A | 12/1996 | Hart et al. |
| 5,607,397 A | 3/1997 | Stephens et al. |
| 5,613,663 A | 3/1997 | Schmidt et al. |
| 5,628,732 A | 5/1997 | Antoon, Jr. et al. |
| 5,634,908 A | 6/1997 | Loomas |
| 5,657,963 A | 8/1997 | Hinchliffe et al. |
| 5,662,615 A | 9/1997 | Blake, III |
| 5,676,657 A | 10/1997 | Yoon |
| 5,709,664 A | 1/1998 | Vandenbroek et al. |
| 5,720,759 A | 2/1998 | Green et al. |
| 5,752,938 A | 5/1998 | Flatland et al. |
| 5,755,702 A | 5/1998 | Hillstead et al. |
| 5,779,697 A | 7/1998 | Glowa et al. |
| 5,782,817 A | 7/1998 | Franzel et al. |
| 5,792,113 A | 8/1998 | Kramer et al. |
| 5,820,600 A | 10/1998 | Carlson et al. |
| 5,820,604 A | 10/1998 | Fox et al. |
| 5,820,606 A | 10/1998 | Davis et al. |
| 5,865,817 A | 2/1999 | Moenning et al. |
| 5,868,714 A | 2/1999 | Danks |
| 5,871,471 A | 2/1999 | Ryan et al. |
| 5,906,595 A | 5/1999 | Powell et al. |
| 5,989,224 A | 11/1999 | Exline et al. |
| 5,993,471 A | 11/1999 | Riza et al. |
| 6,000,670 A | 12/1999 | Okamoto |
| 6,030,403 A | 2/2000 | Long et al. |
| RE36,702 E | 5/2000 | Green et al. |
| 6,066,117 A | 5/2000 | Fox et al. |
| 6,068,011 A | 5/2000 | Paradis |
| 6,077,249 A | 6/2000 | Dittrich et al. |
| 6,077,288 A | 6/2000 | Shimomura et al. |
| 6,083,203 A | 7/2000 | Yoon |
| 6,093,176 A | 7/2000 | Dennis |
| 6,110,154 A | 8/2000 | Shimomura et al. |
| 6,123,689 A | 9/2000 | To et al. |
| 6,159,182 A | 12/2000 | Davis et al. |
| 6,176,843 B1 | 1/2001 | DiCaprio et al. |
| 6,197,002 B1 | 3/2001 | Peterson |
| 6,217,555 B1 | 4/2001 | Hart et al. |
| 7,083,626 B2 * | 8/2006 | Hart et al. ............ 606/108 |
| 7,169,130 B2 | 1/2007 | Exline et al. |
| 2004/0111060 A1 | 6/2004 | Racenet et al. |
| 2004/0204682 A1 | 10/2004 | Smith |
| 2005/0212221 A1 | 9/2005 | Smith et al. |
| 2006/0217665 A1 * | 9/2006 | Prosek ............ 604/167.02 |
| 2006/0217666 A1 | 9/2006 | Wenchell |
| 2006/0224120 A1 | 10/2006 | Smith et al. |
| 2007/0004968 A1 * | 1/2007 | Bonadio et al. ............ 600/208 |

FOREIGN PATENT DOCUMENTS

| | | |
|---|---|---|
| WO | WO 94/07552 | 4/1994 |
| WO | WO 95/05207 | 2/1995 |
| WO | WO 02/41795 | 5/2002 |

* cited by examiner

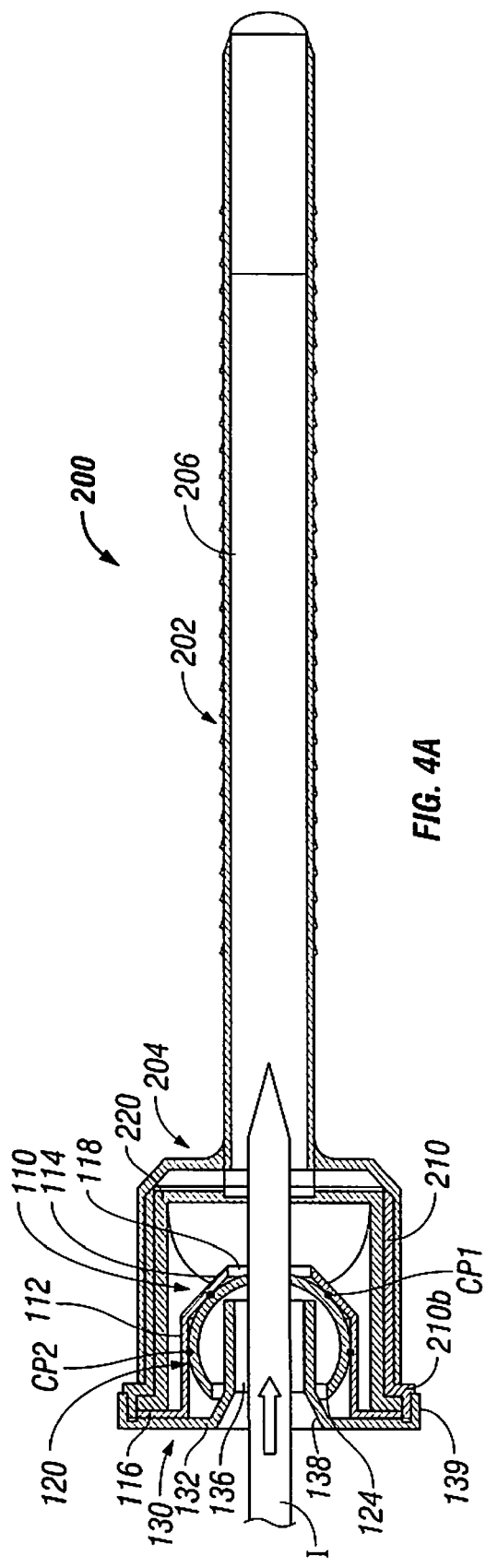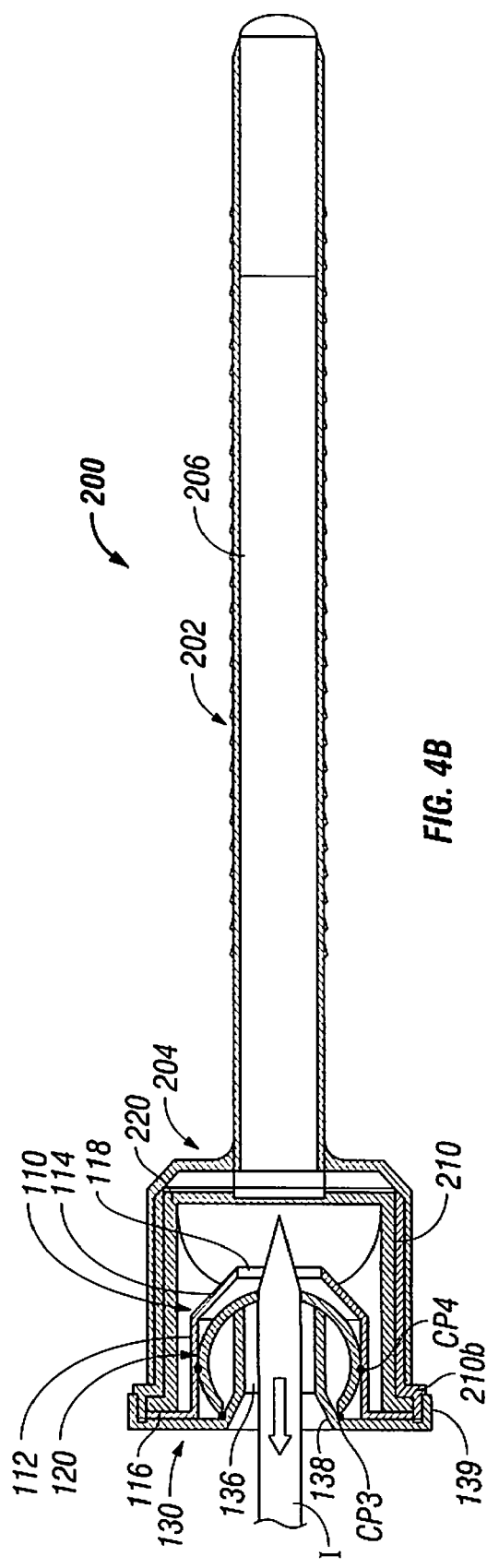

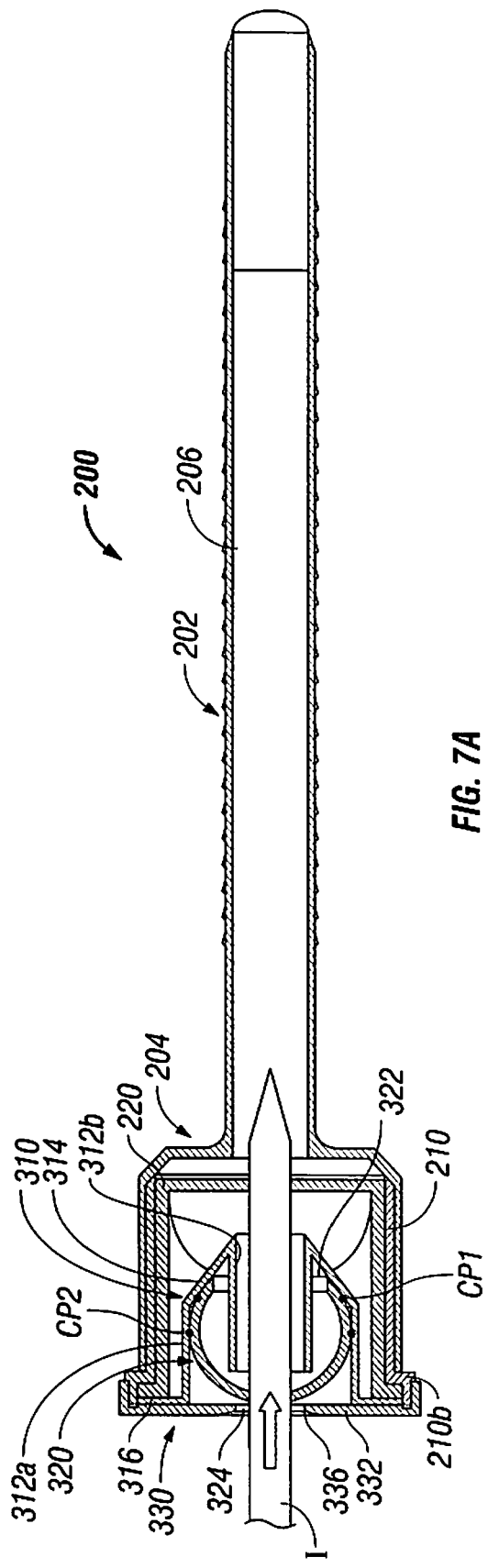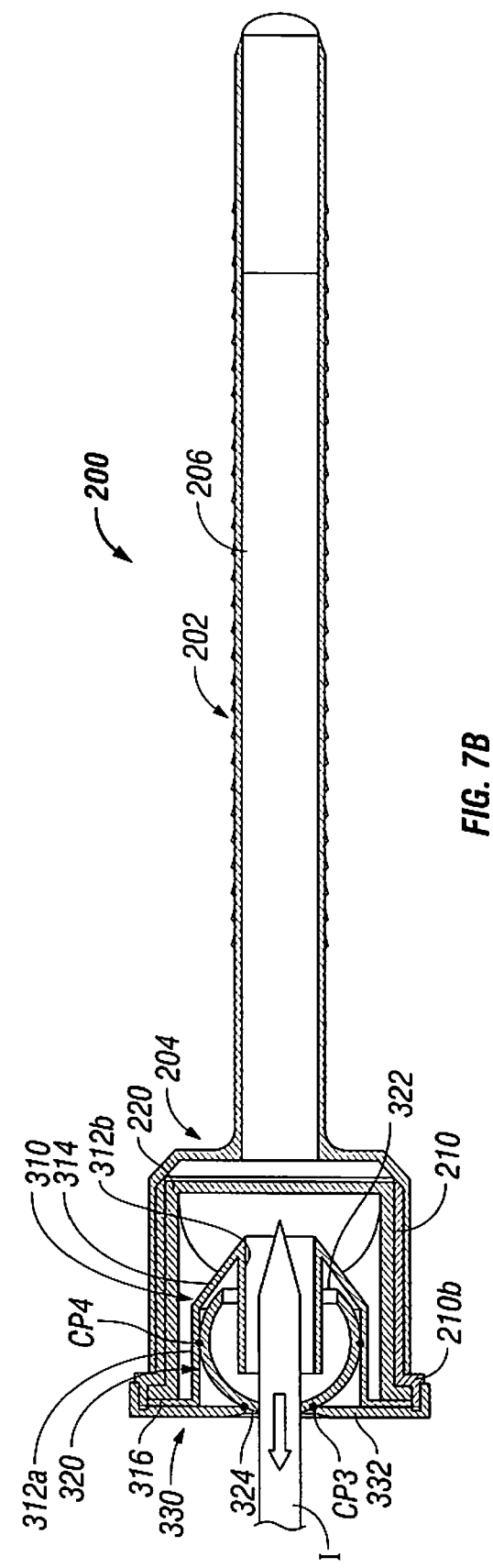

SEAL ASSEMBLY FOR SURGICAL ACCESS DEVICE

BACKGROUND

1. Technical Field

The present disclosure relates to seal assemblies adapted to permit the introduction of surgical instrumentation into a patient's body and, more particularly, to seal assemblies for use with an introducer which is intended for insertion into a patient's body, and for receiving an instrument in sealing engagement therewith.

2. Description of Related Art

Minimally invasive and laparoscopic procedures generally require that any instrumentation inserted into the body be sealed, e.g., provisions are made to ensure that gases and/or fluids do not enter or exit the body through an endoscopic incision, such as, for example in surgical procedures where the surgical region is insufflated. For such procedures, the introduction of a tube into anatomical cavities, such as the peritoneal cavity, is usually accomplished by use of a system incorporating a trocar and cannula assembly. Since the cannula is in direct communication with the interior of the peritoneal cavity, insertion of the cannula into an opening in the patient's body to reach the inner abdominal cavity may be adapted to maintain a fluid tight interface between the abdominal cavity and the outside atmosphere. In view of the desire to maintain the atmospheric integrity of the inner area of the cavity, a seal assembly for a cannula, which permits introduction of a wide range of surgical instrumentation and maintains the atmospheric integrity of the inner area of the cavity is desirable. In this regard, there have been a number of attempts in the prior art to achieve such sealing requirements. A difficulty encountered with conventional seal assemblies, however, is the inability of accommodating the wide range of sizes of instrumentation. In addition, angulation and/or manipulation of instrumentation within the cannula often present difficulties with respect to maintaining seal integrity.

SUMMARY

Accordingly, the present disclosure provides a surgical seal assembly for use with a surgical access device. The seal assembly comprises a seal holder including a cylindrical wall portion having a tapered distal portion, wherein the cylindrical wall portion defines a central passage dimensioned to permit passage of a surgical instrument through the seal holder. The seal assembly further comprises a ball seal supported in the central passage of the seal holder. The ball seal includes a distal aperture and a proximal aperture, wherein at least one of the distal and proximal aperture is dimensioned for substantial sealed reception of the surgical instrument. The ball seal is adapted for angular movement relative to a central longitudinal axis of the seal holder upon angulation of the surgical instrument, whereby the ball seal substantially maintains the seal with the surgical instrument. The seal assembly further comprises a seal cover defining an aperture formed in a transverse wall thereof. The seal cover is configured for connection with the seal holder for maintaining the ball seal within the central passage of the seal holder, wherein the proximal aperture of the ball seal is in registration with the aperture of the seal cover.

The ball seal may be fabricated from at least one of a substantially elastomeric and substantially resilient material. The ball seal may create a seal against a surface of the seal holder during passage of the surgical instrument through the seal holder in a first direction. The ball seal may create a seal against a surface of the seal cover during passage of the surgical instrument through the seal holder in a second direction.

The proximal aperture of the ball seal may be larger than the distal aperture of the ball seal. The seal cover may include a cylindrical wall extending from the transverse wall and being configured for positioning in the proximal aperture of the ball seal. The seal cover may further include a sloped portion between the transverse wall and the cylindrical wall.

The distal aperture of the ball seal may be larger than the proximal aperture of the ball seal. The seal holder may include a cylindrical inner wall portion extending proximally from a distal edge of the tapered portion and may be configured for positioning in the distal aperture of the ball seal.

The ball seal may be substantially spherical.

According to another aspect of the present disclosure, a surgical access device is provided. The surgical access device includes a cannula assembly having a sleeve defining a lumen and supporting a closure valve at a proximal end thereof; and a seal assembly supported at a proximal end of the cannula assembly.

The seal assembly comprises a seal holder including a cylindrical wall portion having a tapered distal portion, wherein the cylindrical wall portion defines a central passage dimensioned to permit passage of a surgical instrument through the seal holder and into the lumen of the cannula assembly. The seal assembly further comprises a ball seal supported in the central passage of the seal holder. The ball seal includes a distal aperture and a proximal aperture, wherein at least one of the distal and proximal aperture is dimensioned for substantial sealed reception of the surgical instrument. The ball seal is adapted for angular movement relative to a central longitudinal axis of the seal holder upon angulation of the surgical instrument, whereby the ball seal substantially maintains the seal with the surgical instrument. The seal assembly further comprises a seal cover defining an aperture formed in a transverse wall thereof. The seal cover is configured for connection with the seal holder for maintaining the ball seal within the central passage of the seal holder, wherein the proximal aperture of the ball seal is in registration with the aperture of the seal cover.

The cannula assembly may include a cannula housing supported on a proximal end of the sleeve. The cannula housing may be configured to support the closure valve therein and is configured to selectively engage the seal assembly.

The cannula housing may include a port opening formed therein and is configured for operative receipt of a luer fitting therein.

According to another aspect of the present disclosure, a surgical seal assembly for use with a surgical access device is provided. The seal assembly may include a cannula assembly including a cannula sleeve defining a central passage dimensioned to permit passage of a surgical instrument through the cannula sleeve; and a substantially spherical seal member defining a proximal opening and a distal opening and a non-cylindrical bore providing communication therethrough between the proximal and distal openings. The substantially spherical seal member may have an outer diameter, and the distal and proximal openings may be smaller than the outer diameter. At least one of the distal and proximal opening may be dimensioned for substantial sealed reception of the surgical instrument. The seal member may be adapted for angular movement relative to a central longitudinal axis of the cannula sleeve upon angulation of the surgical instrument, whereby the seal member substantially maintains the seal with the surgical instrument.

According to another aspect of the present disclosure, a surgical seal assembly for use with a surgical access device is provided. The seal assembly may include a cannula assembly including a cannula sleeve defining a central passage dimensioned to permit passage of a surgical instrument through the cannula sleeve; and a substantially spherical seal member having an outer diameter and defining a proximal opening and a distal opening, wherein the distal and proximal openings are smaller than the outer diameter. The seal member may define a non-cylindrical bore providing communication therethrough between the proximal and distal openings.

BRIEF DESCRIPTION OF THE DRAWINGS

The foregoing features of the present disclosure will become more readily apparent and will be better understood by referring to the following detailed description of preferred embodiments, which are described hereinbelow with reference to the drawings wherein:

FIG. 4A is a longitudinal, cross-sectional view of the cannula and seal assemblies of FIGS. 1 and 2, as taken through 4-4 of FIG. 2 with an instrument being inserted therein and with a ball seal of the seal assembly being shown in a distal position;

FIG. 4B is a longitudinal, cross-sectional view of the cannula and seal assemblies of FIGS. 1 and 2, as taken through 4-4 of FIG. 2 with the instrument being withdrawn therefrom and the ball seal of the seal assembly being shown in a proximal position;

FIG. 7A is a longitudinal, cross-sectional view of the cannula and seal assemblies of FIG. 6, as taken through 7-7 of FIG. 6 with an instrument being inserted therein and with a ball seal of the seal assembly being shown in a distal position;

FIG. 7B is a longitudinal, cross-sectional view of the cannula and seal assemblies of FIG. 6, as taken through 7-7 of FIG. 6 with the instrument being withdrawn therefrom and the ball seal of the seal assembly being shown in a proximal position;

DETAILED DESCRIPTION OF EMBODIMENTS

Figure 1:
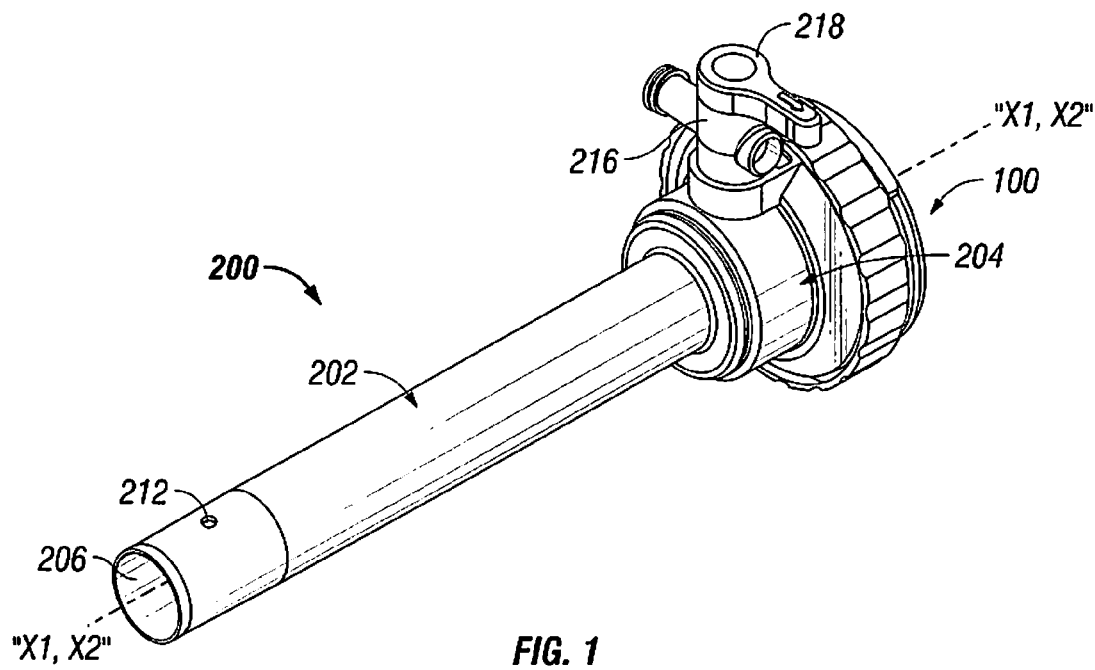
FIGS. 1 and 2 are perspective views of a cannula assembly and a seal assembly in accordance with the principles of the present disclosure.
Figure 2:
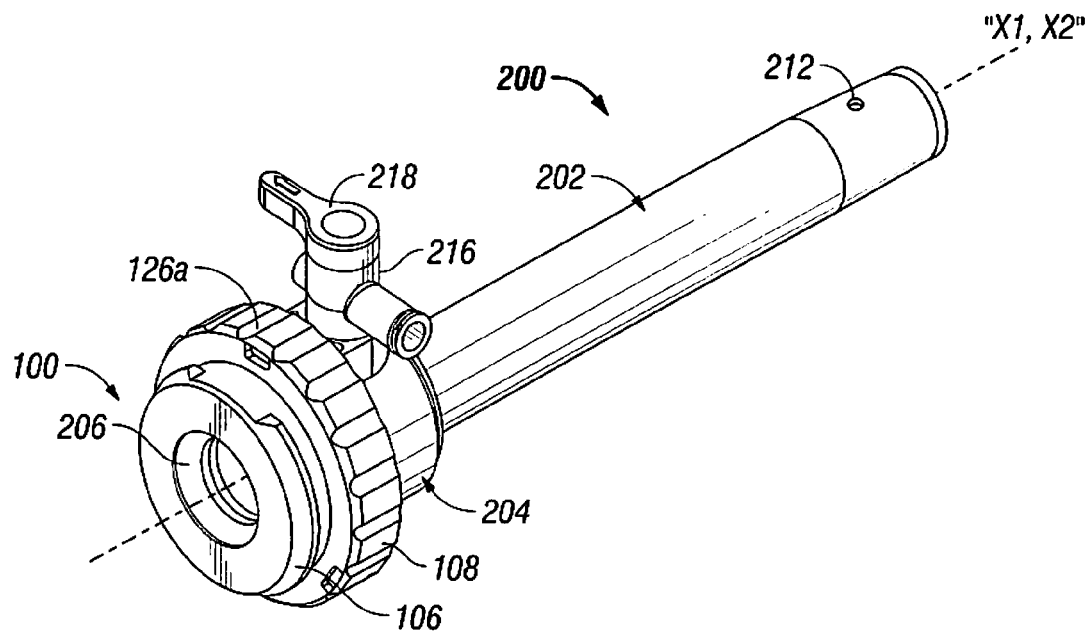
Figure 3:
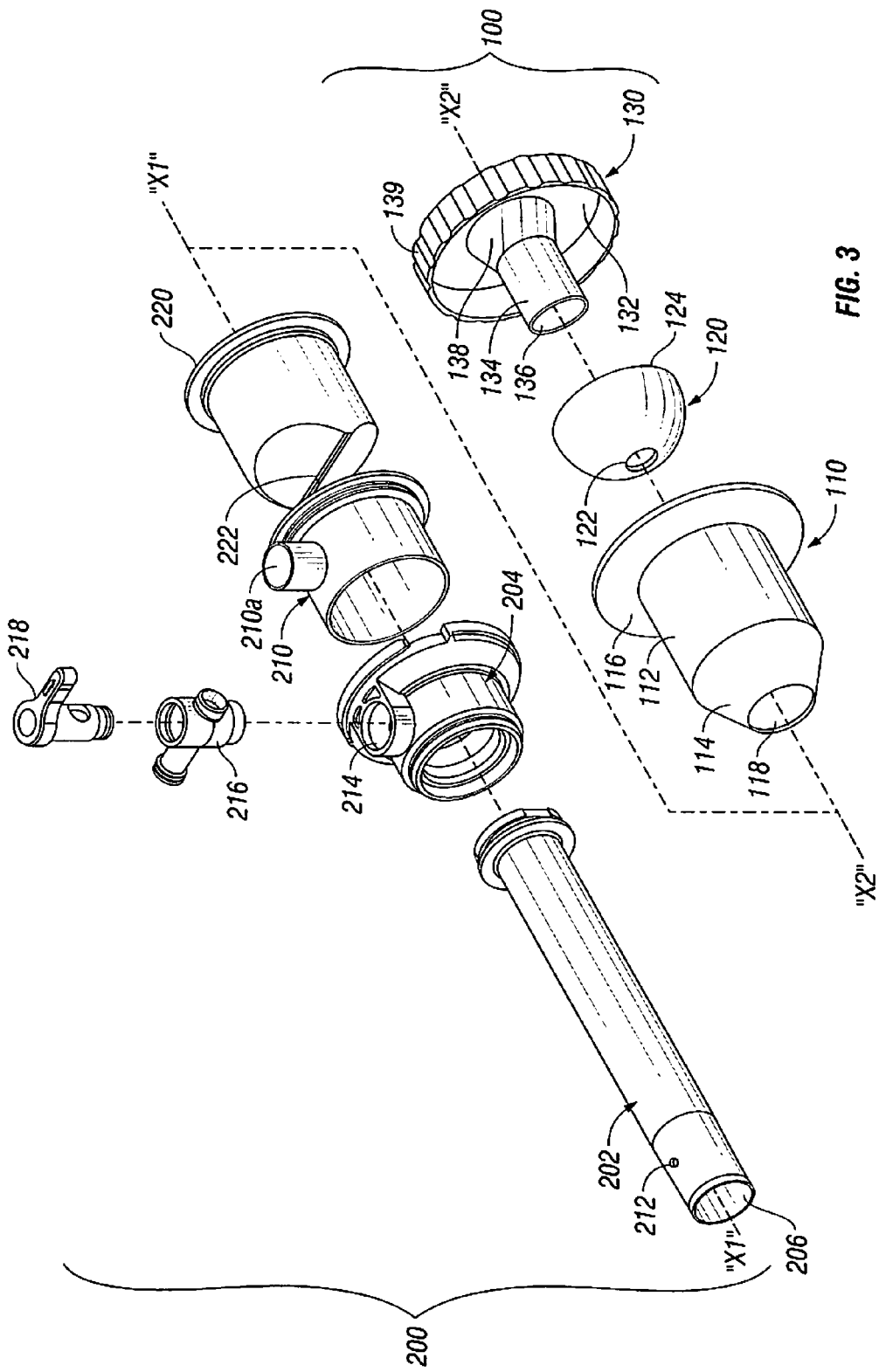
FIG. 3 is a perspective view, with parts separated, of the cannula and seal assemblies of FIGS. 1 and 2.

The seal assembly of the present disclosure, either alone or in combination with a seal system internal to a cannula assembly, provides a substantial seal between a body cavity of a patient and the outside atmosphere before, during and after insertion of an instrument through the cannula assembly. Moreover, the seal assembly of the present invention is capable of accommodating instruments of varying diameters, e.g., from about 5 mm to about 15 mm, by providing a gas tight seal with each instrument when inserted. The flexibility of the present seal assembly greatly facilitates endoscopic surgery where a variety of instruments having differing diameters are often needed during a single surgical procedure.

The seal assembly contemplates the introduction and manipulation of various types of instrumentation adapted for insertion through a trocar and/or cannula assembly while maintaining a fluid tight interface about the instrumentation to preserve the atmospheric integrity of a surgical procedure from gas and/or fluid leakage. Specifically, the seal assembly accommodates angular manipulation of the surgical instrument relative to the seal housing axis. This feature of the present disclosure desirably minimizes the entry and exit of gases and/or fluids to/from the body cavity. Examples of instrumentation include clip appliers, graspers, dissectors, retractors, staplers, laser probes, photographic devices, endoscopes and laparoscopes, tubes, and the like. Such instruments will be collectively referred to herein as "instruments or instrumentation".

By virtue of its features, the seal assembly further defines a substantially reduced profile when assembled together and mounted to a cannula assembly. This reduced profile advantageously increases the working length of instruments introduced into the body cavity through the cannula assembly. In addition, the reduced profile permits enhanced angulation of a surgical instrument relative to the seal housing axis.

In the following description, as is traditional the term "proximal" refers to the portion of the instrument closest to the operator while the term "distal" refers to the portion of the instrument remote from the operator.

Referring now to the drawings, in which like reference numerals identify identical or substantially similar parts throughout the several views, FIGS. 1-5 illustrate the seal assembly 100 of the present disclosure mounted to cannula assembly 200. Cannula assembly 200 may be any conventional cannula suitable for the intended purpose of accessing a body cavity and permit introduction of instruments therethrough. Cannula assembly 200 is particularly adapted for use in laparoscopic surgery where the peritoneal cavity is insufflated with a suitable gas, e.g., $CO_2$, to raise the cavity wall from the internal organs therein. Cannula assembly 200 is typically used with an obturator assembly (not shown) which is a sharp pointed instrument positionable within the passageway of the cannula assembly 200. The obturator assembly is utilized to penetrate the abdominal wall and then subsequently removed from the cannula assembly 200 to permit introduction of the surgical instrumentation utilized to perform the procedure.

With reference to FIGS. 1-5B, cannula assembly 200 includes cannula sleeve 202 and cannula housing 204 mounted to an end of the sleeve 202. Any suitable means, known in the art, for mounting cannula sleeve 202 to cannula housing 204 are envisioned including threaded arrangements, bayonet coupling, snap-fit arrangements, adhesives, etc. Cannula sleeve 202 and cannula housing 204 may be integrally formed. Cannula sleeve 202 defines a longitudinal "X1" axis extending along the length of sleeve 202. Sleeve 202 further defines an internal longitudinal lumen passage 206 dimensioned to permit passage of surgical instrumentation therethrough.

Adjacent a distal end of cannula sleeve 202 is formed an aperture 212 which extends through the wall of sleeve 202 and is in fluid communication with lumen 206 of sleeve 202. Aperture 212 permits passage of insufflation gases through cannula sleeve 202 during the surgical procedure.

Sleeve 202 may be formed of stainless steel or other rigid materials such as a polymeric material or the like. Sleeve 202 may be clear or opaque. The diameter of sleeve 202 may vary, but, typically ranges from about 10 mm to about 15 mm for use with the seal assembly 100 of the present disclosure.

Cannula housing 204 includes port opening 214 (FIG. 3) and luer fitting 216 positioned within the port opening 214. Luer fitting 216 is adapted for connection to a supply of insufflation gaseous is conventional in the art and incorporates valve 218 to selectively open and close the passage of the luer fitting 216.

Cannula housing 204 may include and supports a housing insert 210 therewithin. Housing insert 210 defines a stem 210a extending therefrom and configured for insertion or placement within port opening 214 of cannula housing 204.

Cannula housing 204 further includes and supports duckbill or zero closure valve 220 configured for positioning within housing insert 210. Closure valve 220 tapers distally and inwardly to a sealed configuration. Closure valve 220 defines a slit 222 which opens to permit passage of the surgical instrumentation and closes in the absence of the instrumentation. Closure valve 220 is preferably adapted to close upon exposure to the forces exerted by the insufflation gases in the internal cavity. Other zero closure valves are also contemplated including single or multiple slit valve arrangements, trumpet valves, flapper valves, etc. Closure valve 220 rests upon an internal shelf 210b of housing insert 210 when assembled.

With continued reference to FIGS. 1-5B, seal assembly 100 will be discussed in detail. Seal assembly 100 may be a separate component from cannula assembly 200 and, accordingly, adapted for releasable connection to the cannula assembly 200. Alternatively, seal assembly 100 may be incorporated as part of cannula assembly 200.

Seal assembly 100 includes a seal housing or holder 110, a ball seal 120, and a seal cover 130. Seal assembly 100 defines central seal axis "X2" which is preferably parallel to the axis "X1" of cannula sleeve 202 and, more specifically, coincident with the axis "X1" of the cannula sleeve 202.

Seal housing or holder 110 includes a cylindrical wall portion 112 having a tapered distal portion 114 and a transverse annular wall or flange 116 extending from a proximal end thereof. Seal holder 110 defines central passage 118 which is dimensioned to receive a surgical instrument and laterally confine ball seal 120.

Figure 4:
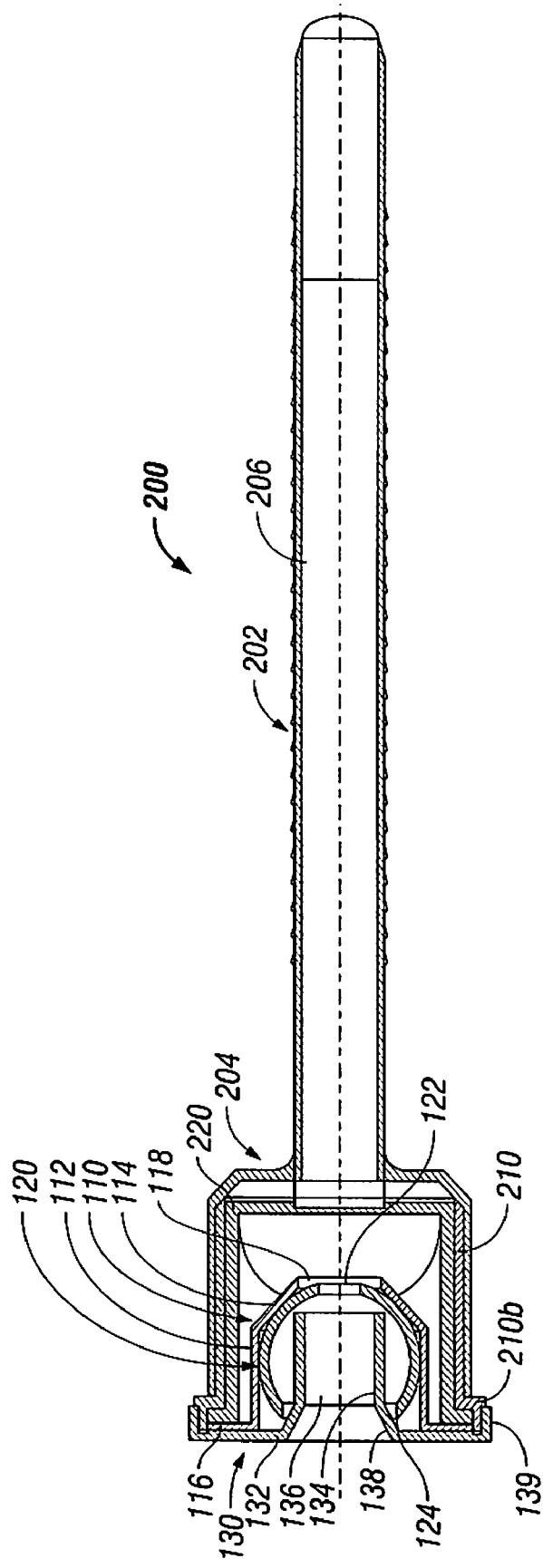
FIG. 4 is a longitudinal, cross-sectional view of the cannula and seal assemblies of FIGS. 1 and 2, as taken through 4-4 of FIG. 2.
Figure 5:
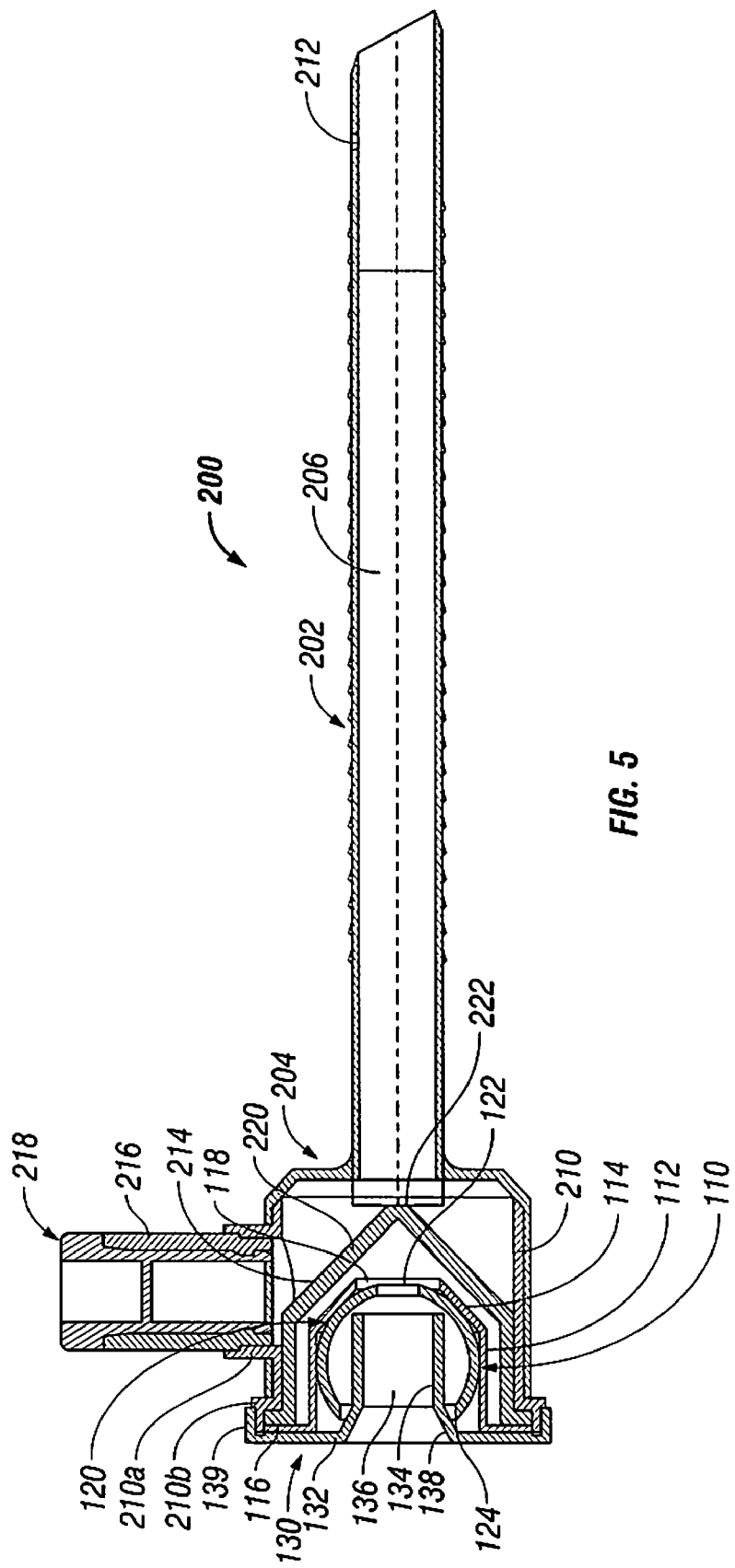
FIG. 5 is a longitudinal, cross-sectional view of the cannula and seal assemblies of FIGS. 1 and 2, as taken through 5-5 of FIG. 2.

As best shown in FIGS. 4 and 5, tapered distal portion 114 is obliquely arranged relative to seal holder axis "X2" and extends radially inwardly relative thereto in a distal direction. Tapered distal portion 114 assists in creating a seal in combination with ball seal 120, when the instrument is introduced into cannula assembly 200, as will be discussed in greater detail below.

Ball seal 120 has a substantially spherical profile and includes a distal aperture 122 and a proximal aperture 124. Distal aperture 122 has a diameter which is relatively smaller than proximal aperture 124. Ball seal 120 has a diameter substantially equal or smaller than a diameter of cylindrical wall portion 112 of seal holder 110 such that ball seal 120 may be seated within central passage 118 of seal holder 110. Distal aperture 122 and proximal aperture 124 may share a common central axis.

Ball seal 120 may be fabricated from a suitable resilient and/or elastomeric material, such as, for example, natural rubber, polyisoprene.

Seal cover 130 includes a transverse wall 132, a cylindrical wall 134 depending in a distal direction from transverse wall 132 and defining a central lumen or passage 136. Seal cover 130 defines a sloped or angled portion 138 between transverse wall 132 and cylindrical wall 134. Cylindrical wall 134 is dimensioned for receipt within proximal aperture 124 of ball seal 120. Cylindrical wall 134 is further dimensioned such that a distal edge thereof terminates at a location proximal of a distal edge of seal holder 110.

Sloped portion 138 is obliquely arranged relative to seal housing axis "X2" and extends radially inwardly relative to the seal holder axis "X2" in the distal direction. Sloped portion 138 assists in guiding the inserted instrument into lumen 206 of cannula assembly 200, particularly, when the instrument is non-aligned or off-axis relative to the seal holder axis "X2", or introduced at an angle relative to the seal holder axis "X2". Sloped portion 138 provides more flexibility to the surgeon by removing the necessity that the instrument be substantially aligned with the seal holder axis "X2" upon insertion.

Seal cover 130 may include an outer wall 139 configured for selective engagement with cannula housing 204 in order to secure seal assembly 100 to cannula assembly 200.

Figure 5A:
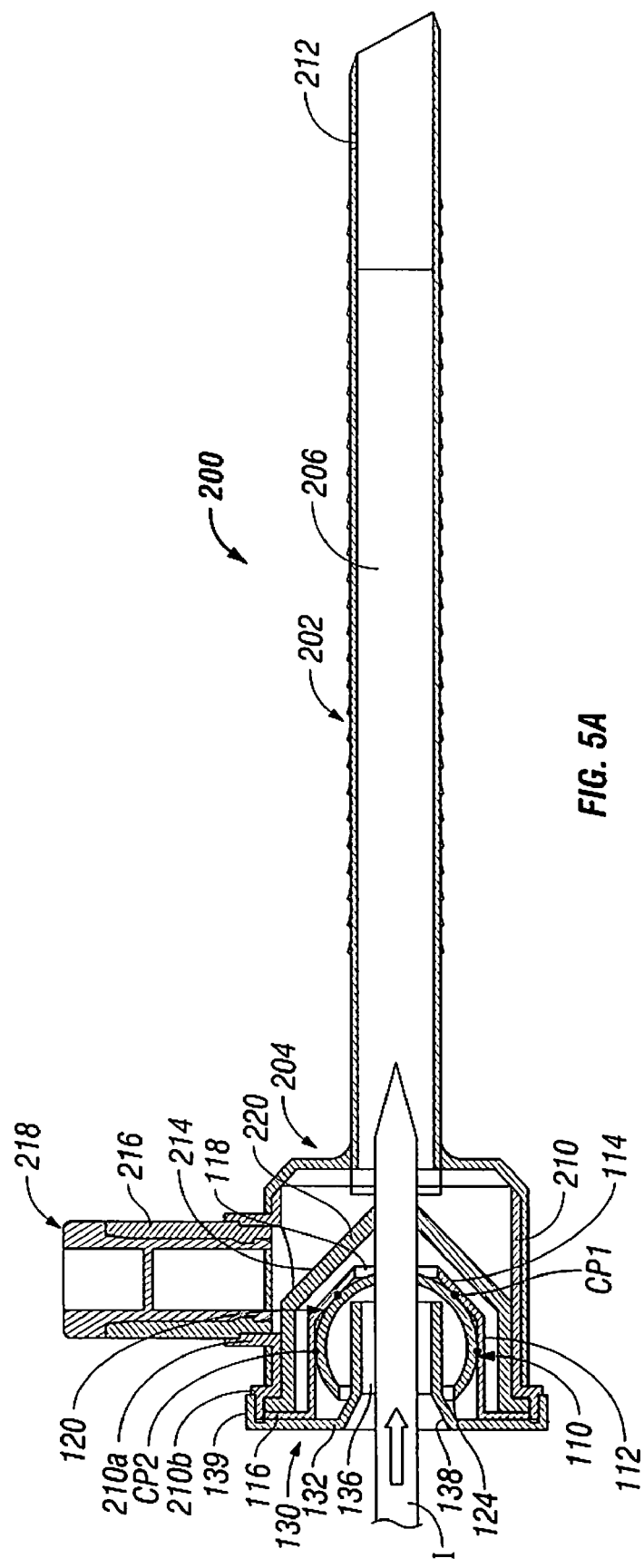
FIG. 5A is a longitudinal, cross-sectional view of the cannula and seal assemblies of FIGS. 1 and 2, as taken through 5-5 of FIG. 2 with the instrument being inserted therein and with the ball seal of the seal assembly being shown in the distal position.

When seal assembly 100 is assembled, ball seal 120 of seal assembly 100 is interposed between seal holder 110 and seal cover 130. In particular, ball seal 120 is slidably and rotatably interposed between seal holder 110 and seal cover 130 so as to translate in an axial direction and rotate about longitudinal axis "X1, X2". In particular, ball seal 120 may translate distally to a distal position in response to insertion of an instrument "I" through the seal assembly 100 such that ball seal 120 contacts seal holder 110 and forms two annular seals therewith. As best shown in FIGS. 4A and 5A, ball seal 120 engages the tapered distal portion 114 of seal holder 110 at annular contact point CP1 and engages cylindrical wall portion 112 at annular contact point CP2. Annular contact points CP1 and CP2 are merely illustrative of the specific points of the annular seals that ball seal 120 engages in the respective cross-sectional views shown by FIGS. 4A and 5A. Nonetheless, ball seal 120 engages the seal holder 110 such that ball seal 120 is in circumferential contact with the seal holder 110 at a plurality of annular contact points that form the annular seals described above.

With continued reference to FIG. 4A, in use and during insertion into cannula assembly 200 of an instrument having a diameter greater than the diameter of distal aperture 122 of ball seal 120, as the instrument "I" is inserted into and through central lumen 136 of seal cover 130, the instrument "I" passes through distal aperture 122 of ball seal 120. The frictional force or resistance of ball seal 120 along the outer surface of the instrument "I", as the instrument "I" is advanced into lumen 206 of cannula assembly 200, causes ball seal 120 to translate distally and contact or seal against a surface of seal holder 110, e.g., against an inner surface of tapered distal portion 114 of seal holder 110, as seen in FIGS. 4A and 5A and as discussed above.

Figure 5B:
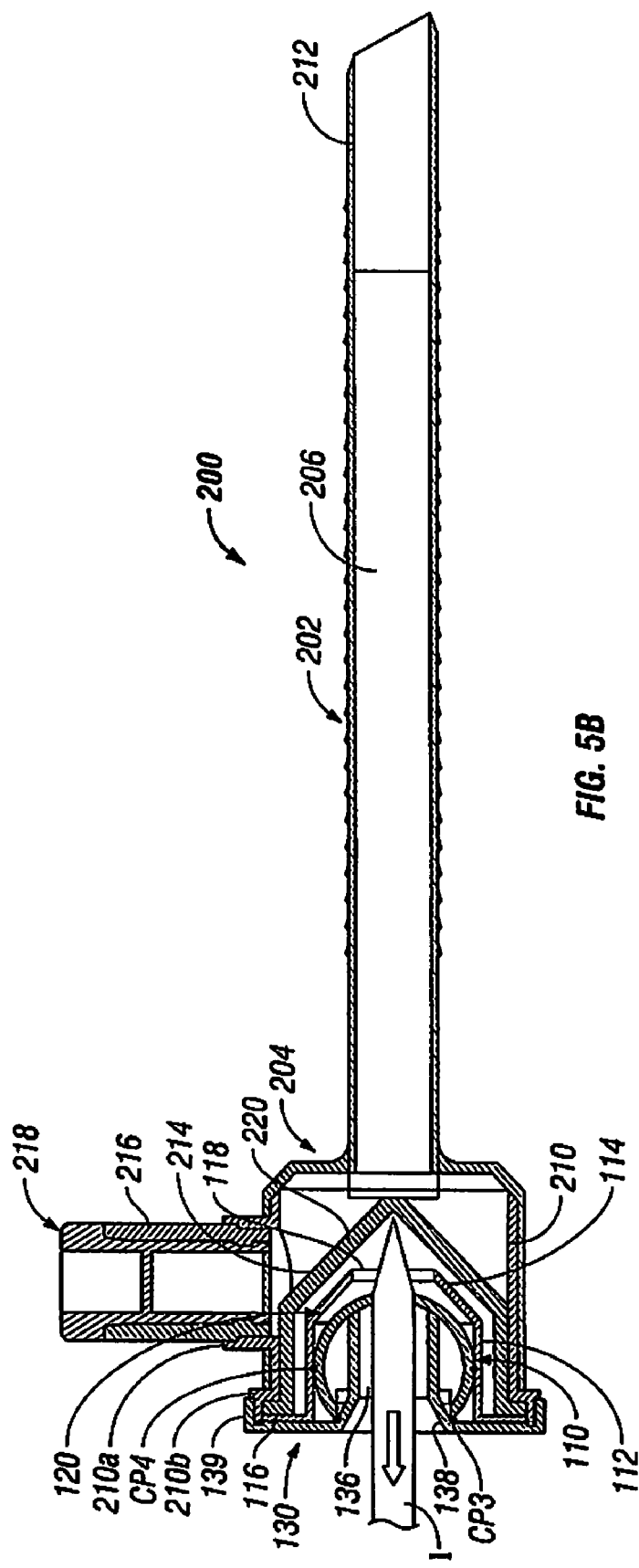
FIG. 5B is a longitudinal, cross-sectional view of the cannula and seal assemblies of FIGS. 1 and 2, as taken through 5-5 of FIG. 2 with the instrument being withdrawn therefrom and the ball seal of the seal assembly being shown in the proximal position.
Figure 6:
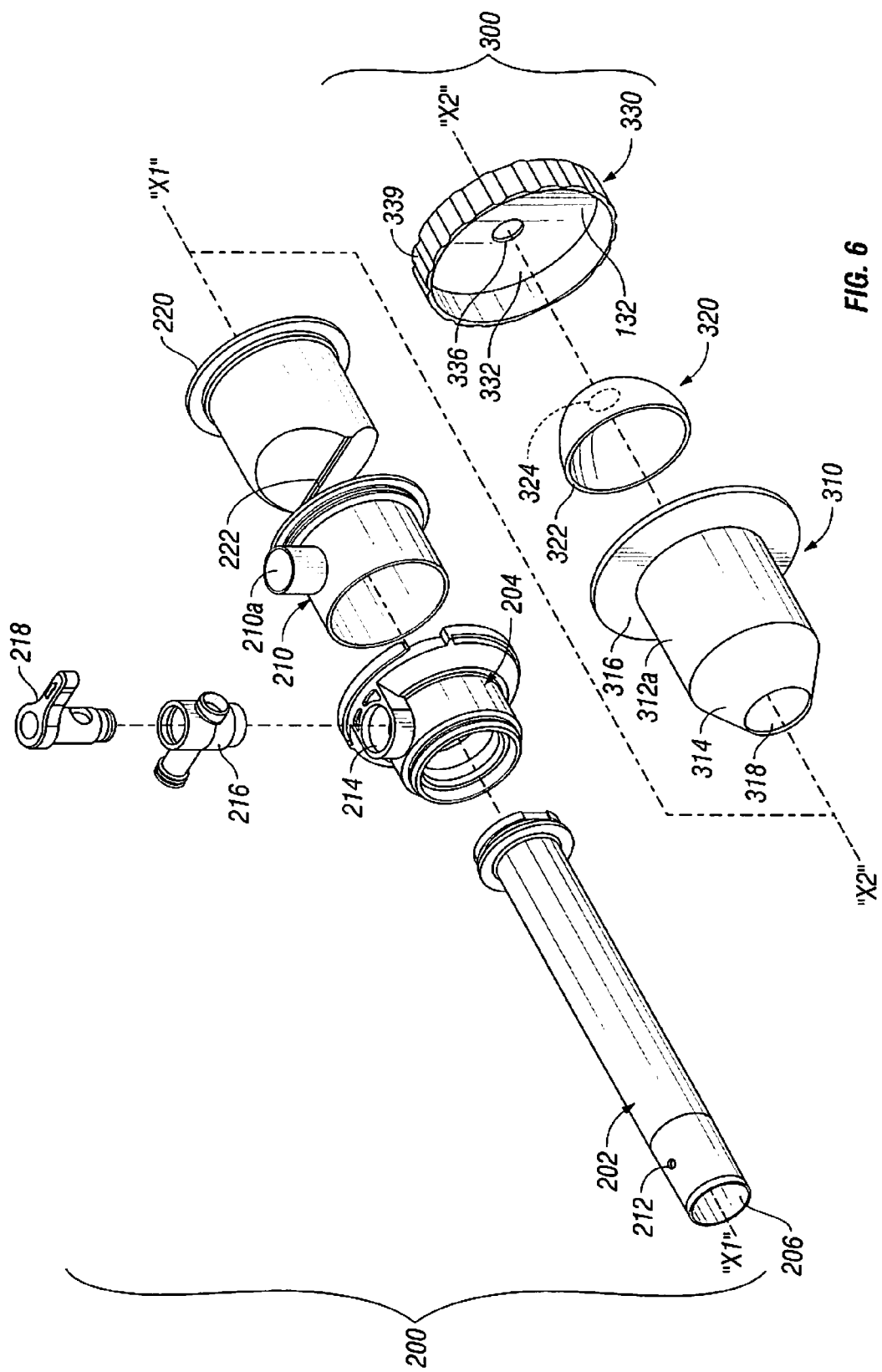
FIG. 6 is a perspective view, with parts separated, of a cannula assembly and a seal assembly according to an alternate embodiment of the present disclosure.

Further and during withdrawal of the instrument "I" from cannula assembly 200, the frictional force or resistance of ball seal 120 along the outer surface of the instrument "I" as the instrument "I" is withdrawn from lumen 206 of cannula assembly 200 causes ball seal 120 to translate proximally to a proximal position where ball seal 120 contacts or seals against a surface of seal cover 130, e.g., against an inner surface of transverse wall 132 and/or against a distal edge of cylindrical wall 134, and/or against a surface of seal holder 110, e.g., against cylindrical wall portion 112 of seal holder 110. In this manner, ball seal 120 forms an annular seal with seal cover 130 and an annular seal with seal holder 110. As best shown in FIGS. 4B and 5B, ball seal 120 engages the inner surface of transverse wall 132 and/or against a distal edge of cylindrical wall 134 at annular contact point CP3 and engages cylindrical wall portion 112 of seal holder 110 at annular contact point CP4. Annular contact points CP3 and CP4 are merely illustrative of the specific points of the annular seals that ball seal 120 engages in the respective cross-sectional views shown by FIGS. 4B and 5B. Nonetheless, ball seal 120 engages seal cover 130 and seal holder 110 such that ball seal 120 is in circumferential contact with seal cover 130 and seal holder 110. In this respect, ball seal 120 is in circumferential contact at a plurality of annular contact points that form the annular seals described above.

Turning now to FIGS. 6-8B, a seal assembly, according to an alternate embodiment of the present disclosure, for use with cannula assembly 200 is generally designated as 300. Seal assembly 300 is substantially similar to seal assembly 100 and thus will only be discussed in detail herein to the extent necessary to identify differences in construction and operation thereof.

Seal assembly 300 includes a seal housing or holder 310, a ball seal 320, and a seal cover 330.

Seal housing or holder 310 includes a cylindrical outer wall portion 312*a* having a tapered distal portion 314, a cylindrical inner wall portion 312*b* extending proximally from a distal end of tapered distal portion 314, and a transverse annular wall or flange 316 extending from a proximal end thereof. Seal holder 310 defines central passage 318 which is dimensioned to receive a surgical instrument and laterally confine ball seal 320. Cylindrical inner wall portion 312*b* terminates in a free proximal end or edge.

Figure 7:
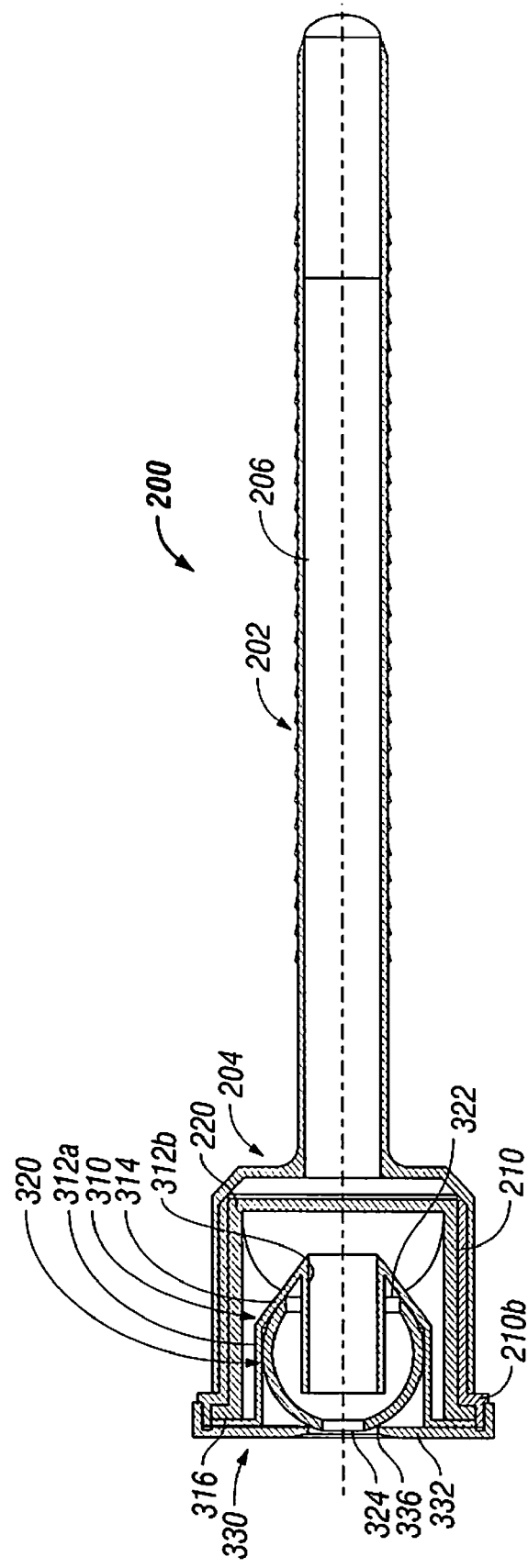
FIG. 7 is a longitudinal, cross-sectional view of the cannula and seal assemblies of FIG. 6, as taken through 7-7 of FIG. 6.
Figure 8:
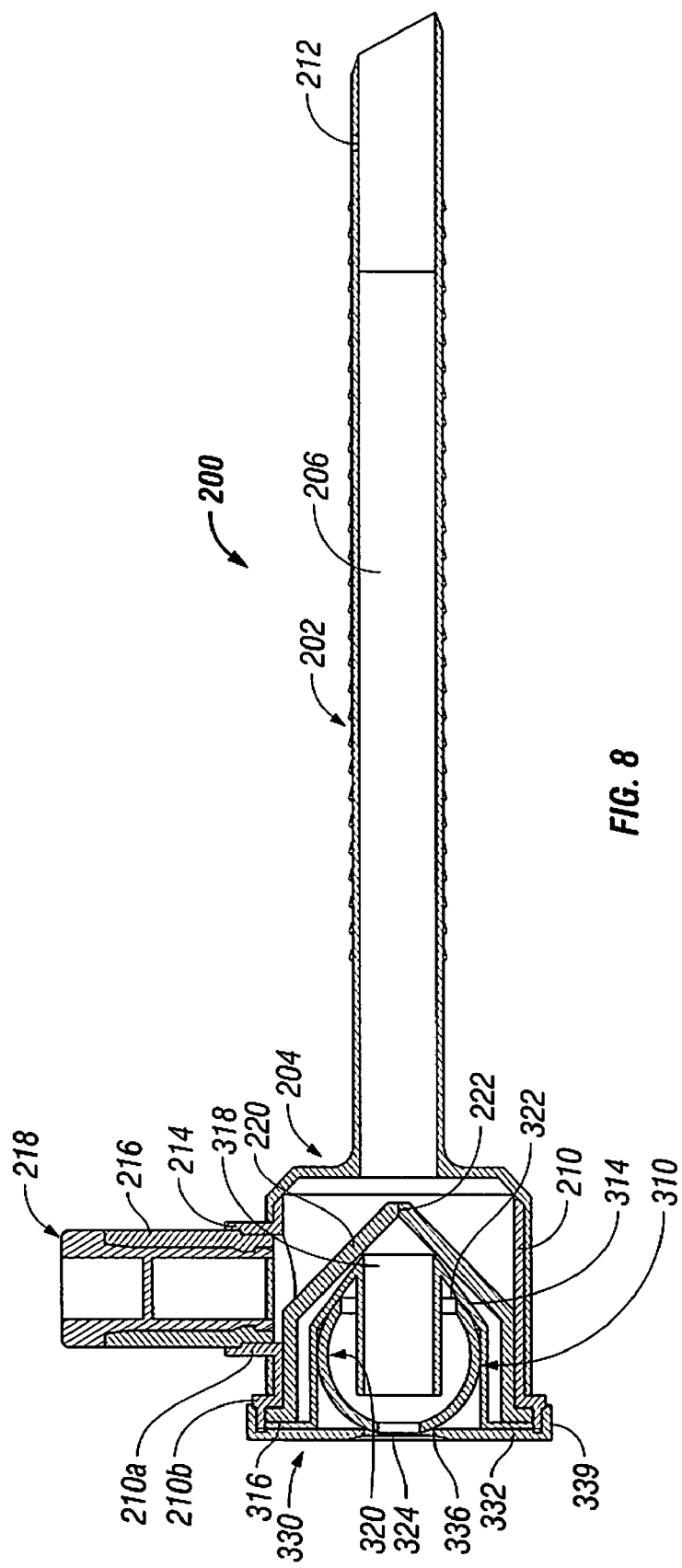
FIG. 8 is a longitudinal, cross-sectional view of the cannula and seal assemblies of FIG. 6, as taken through 8-8 of FIG. 6.

As best shown in FIGS. 7 and 8, tapered distal portion 314 is obliquely arranged relative to seal holder axis "X2" and extends radially inwardly relative thereto in a distal direction. Tapered distal portion 314 assists in creating a seal in combination with ball seal 320, when the instrument is introduced into cannula assembly 200, as will be discussed in greater detail below.

Ball seal 320 has a substantially spherical profile and includes a distal aperture 322 and a proximal aperture 324. Distal aperture 322 has a diameter which is relatively larger than proximal aperture 324. Distal aperture 322 is dimensioned so as to receive cylindrical inner wall portion 318*a* of seal holder 310 therewithin.

Ball seal 320 has a diameter substantially equal to or smaller than a diameter of cylindrical outer wall portion 312*a* of seal holder 310 such that ball seal 320 may be seated within a space defined between cylindrical outer wall portion 312*a* and cylindrical inner wall portion 312*b* of seal holder 310. Distal aperture 322 and proximal aperture 324 of ball seal 320 may share a common central axis.

Seal cover 330 includes a transverse wall 332 defining a central opening 336. Seal cover 330 may included an outer wall 339 configured for selective engagement with cannula housing 204 in order to secure seal assembly 300 to cannula assembly 200.

Figure 8A:
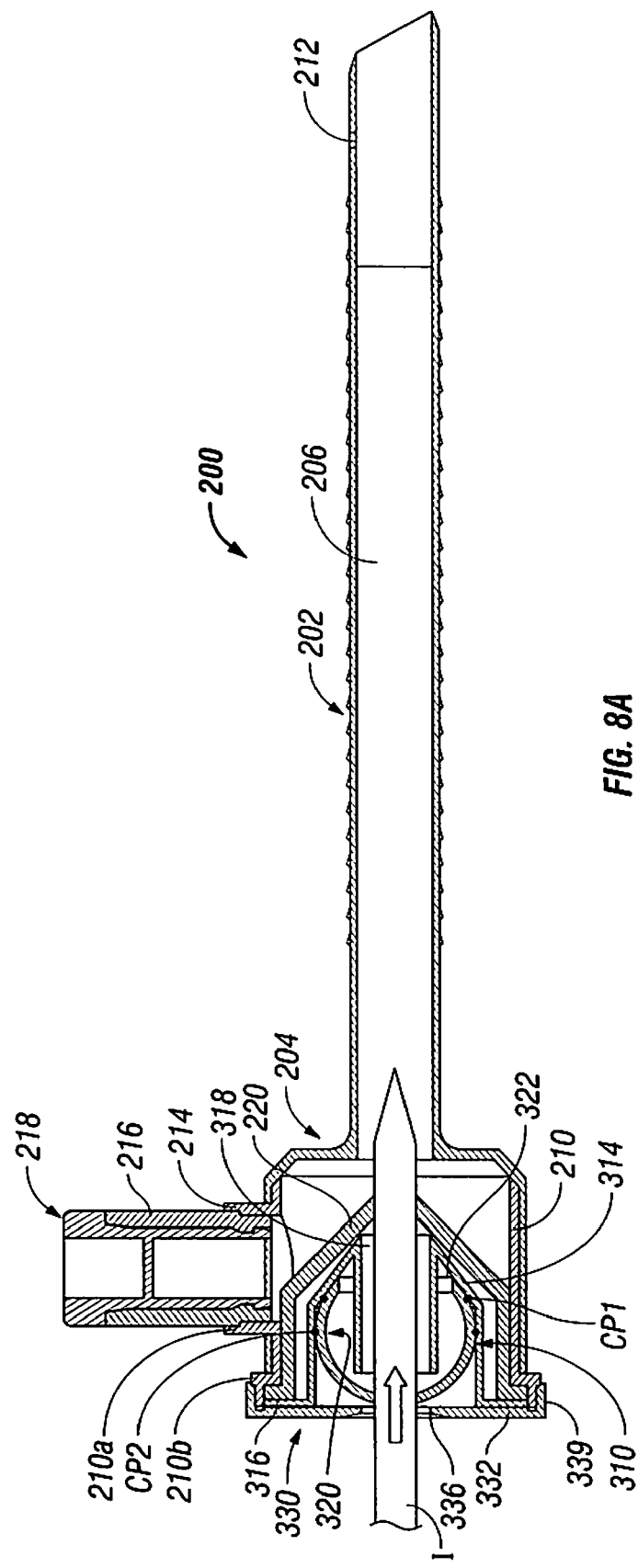
FIG. 8A is a longitudinal, cross-sectional view of the cannula and seal assemblies of FIG. 6, as taken through 8-8 of FIG. 6 with the instrument being inserted therein and with the ball seal of the seal assembly being shown in the distal position.

When seal assembly 300 is assembled, ball seal 320 of seal assembly 300 is interposed between seal holder 310 and seal cover 330. In particular, ball seal 320 is slidably and rotatably interposed between seal holder 310 and seal cover 330 so as to translate in an axial direction and rotate about longitudinal axis "X1, X2". In particular, ball seal 320 may translate distally to a distal position in response to insertion of an instrument "I" through the seal assembly 300 such that ball seal 320 contacts seal holder 310 and forms two annular seals therewith. As best shown in FIGS. 7A and 8A, ball seal 320 engages the tapered distal portion 314 of seal holder 310 at annular contact point CP1 and engages cylindrical wall portion 312 at annular contact point CP2. Annular contact points CP1 and CP2 are merely illustrative of the specific points of the annular seals that ball seal 320 engages in the respective cross-sectional views shown by FIGS. 7A and 8A. Nonetheless, ball seal 320 engages the seal holder 310 such that ball seal 320 is in circumferential contact with the seal holder 310 at a plurality of annular contact points that form the annular seals described above.

With continued reference to FIG. 7A, in use and during insertion into cannula assembly 200 of an instrument, having a diameter greater than the diameter of proximal aperture 324 of ball seal 320, as the instrument "I" is inserted into and through central opening 336 of seal cover 330, the instrument "I" passes through proximal aperture 324 of ball seal 320. The frictional force or resistance of ball seal 320 along the outer surface of the instrument "I", as the instrument "I" is advanced into lumen 206 of cannula assembly 200, causes ball seal 320 to translate distally and contact or seal against at least one surface of seal holder 310, e.g., against an inner surface of tapered distal portion 314 of seal holder 310 and/or against an inner surface of cylindrical outer wall portion 312*a*, as seen in FIGS. 7A and 8A and as discussed above.

Figure 8B:
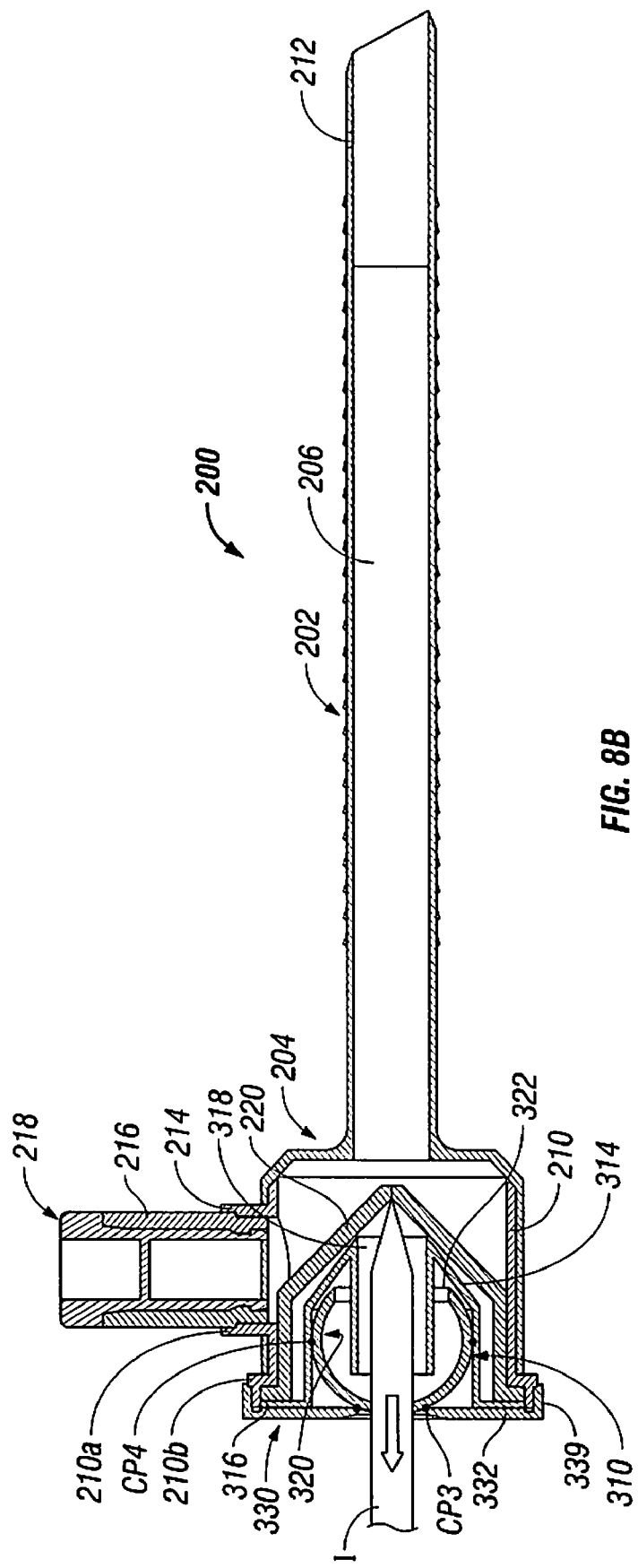
FIG. 8B is a longitudinal, cross-sectional view of the cannula and seal assemblies of FIG. 6, as taken through 8-8 of FIG. 6 with the instrument being withdrawn therefrom and the ball seal of the seal assembly being shown in the proximal position.

Further and during withdrawal of the instrument "I" from cannula assembly 200, the frictional force or resistance of ball seal 320 along the outer surface of the instrument "I", as the instrument "I" is withdrawn from lumen 206 of cannula assembly 200, causes ball seal 320 to translate proximally to a proximal position where ball seal 320 contacts or seals against a surface of seal cover 330, e.g., against an inner surface of transverse wall 332, and/or against a surface of seal holder 310, e.g., against cylindrical wall portion 312 of seal holder 310. In this manner, ball seal 320 forms an annular seal with seal cover 330 and an annular seal with seal holder 310. As best shown in FIGS. 7B and 8B, ball seal 320 engages the inner surface of transverse wall 332 and/or against a distal edge of cylindrical wall 334 at annular contact point CP3 and engages cylindrical wall portion 312 of seal holder 310 at annular contact point CP4. Annular contact points CP3 and CP4 are merely illustrative of the specific points of the annular seals that ball seal 320 engages in the respective cross-sectional views shown by FIGS. 7B and 8B. Nonetheless, ball seal 320 engages seal cover 330 and seal holder 310 such that ball seal 320 is in circumferential contact with seal cover 330 and seal holder 310. In this respect, ball seal 120 is in circumferential contact at a plurality of annular contact points that form the annular seals described above.

Figure 9:
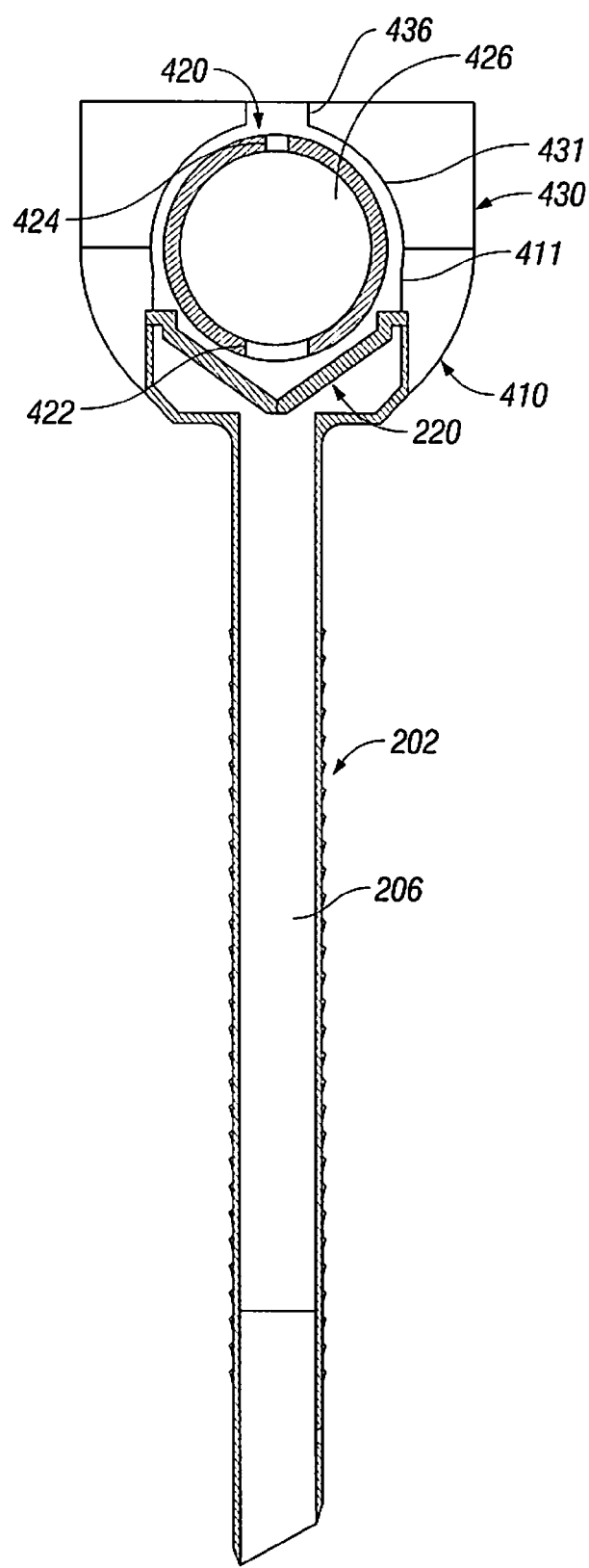
FIG. 9 is a schematic, longitudinal, cross-sectional view of a cannula assembly and a seal assembly according to another embodiment of the present disclosure.

Turning now to FIG. 9, a seal assembly, according to an alternate embodiment of the present disclosure, for use with cannula assembly 200 is generally designated as 400. Seal assembly 400 is substantially similar to seal assembly 100 and thus will only be discussed in detail herein to the extent necessary to identify differences in construction and operation thereof.

Seal assembly 400 includes a seal lower housing 410, a ball seal 420, and a seal upper housing 430. Seal lower housing 410 includes a substantially hemispherical recess 411 formed therein. Seal lower housing 410 is configured for support on an end of sleeve 202 of cannula assembly 200, at a location above or proximal of closure valve 220.

Ball seal 420 has a substantially spherical profile and includes a distal aperture 422 and a proximal aperture 424. Distal aperture 422 has a diameter which is different than proximal aperture 424. As seen in FIG. 9, distal aperture 422 of ball seal 420 may be relatively larger than proximal aperture 424 of ball seal 420. Ball seal 420 defines a hollow cavity, chamber or the like 426.

Seal upper housing 430 includes a transverse wall 432 defining a central opening 436 therein that extends into a substantially hemispherical recess 431. Central opening 436 of seal upper housing 430 is in registration with proximal aperture 424 of ball seal 420. Seal upper housing 430 is configured for connection with seal lower housing 410 such that hemispherical recess 431 thereof is in registration with hemispherical recess 411 of seal lower housing 410.

When seal assembly 400 is assembled, ball seal 420 of seal assembly 400 is interposed between seal lower housing 410 and seal upper housing 430. In particular, ball seal 420 is slidably and rotatably seated within hemispherical recesses 411 and 431 of seal lower housing 410 and seal upper housing 430 so as to translate in an axial direction and rotate about longitudinal axis.

In use and during insertion into cannula assembly 200 of an instrument having a diameter greater than the diameter of proximal aperture 424 of ball seal 420, as the instrument is inserted into and through central aperture 436 of seal upper housing 430, the instrument passes through proximal aperture 424 of ball seal 420. The frictional force or resistance of ball seal 420 along the outer surface of the instrument, as the instrument is advanced into lumen 206 of cannula assembly 200, causes ball seal 420 to contact or seal against at least one surface of seal lower housing 410, e.g., against an inner surface of hemispherical recess 411 of seal lower housing 410.

Further, during withdrawal of the instrument from cannula assembly 200, the frictional force or resistance of ball seal 420 along the outer surface of the instrument, as the instrument is withdrawn from lumen 206 of cannula assembly 200, causes ball seal 420 to contact or seal against a surface of seal upper housing 430, e.g., against an inner surface of hemispherical recess 431 of seal upper housing 430.

Figure 10:
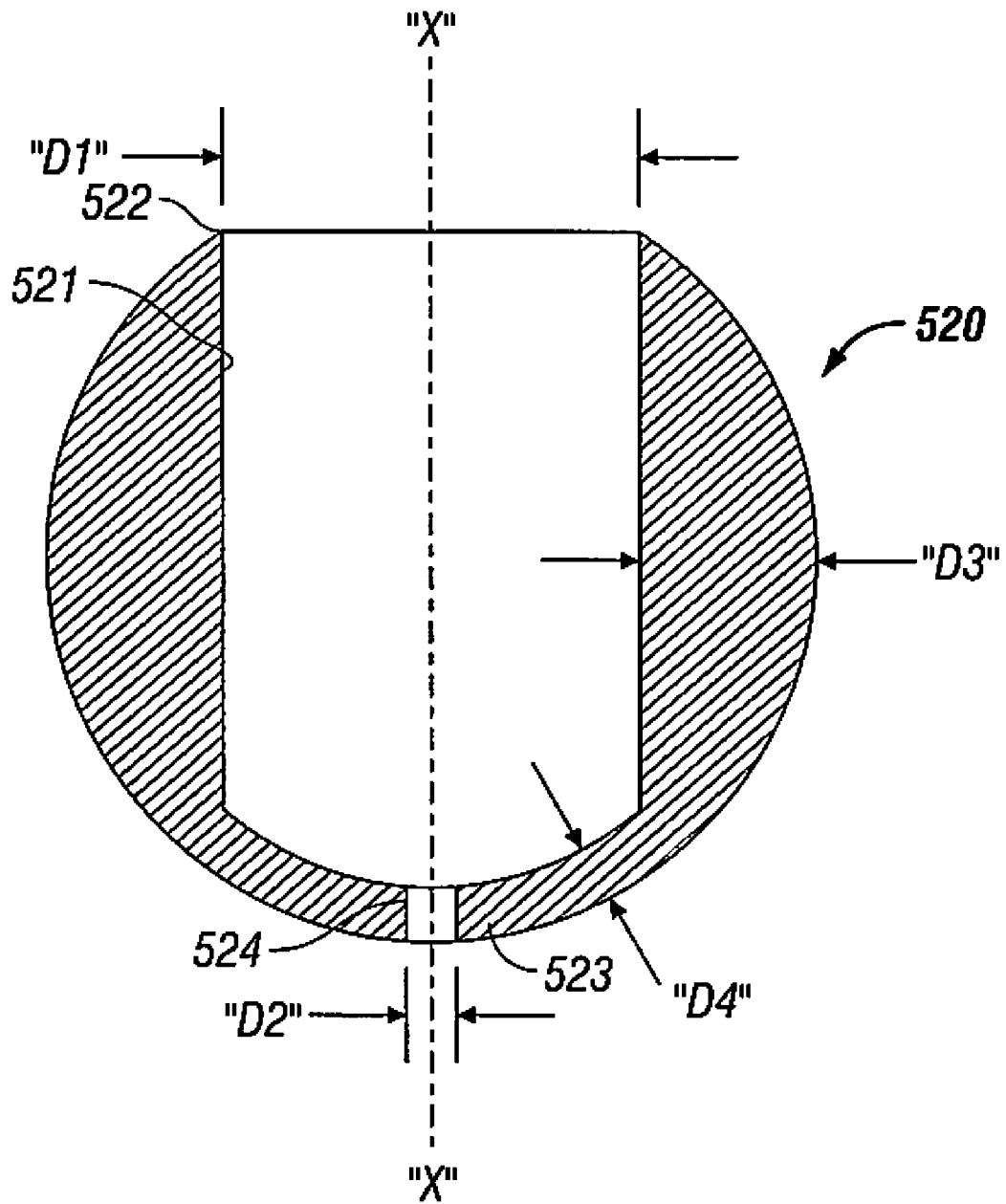
FIG. 10 is a longitudinal, cross-sectional view of a ball seal in accordance with another embodiment of the present disclosure.

Turning now to FIG. 10, a ball seal, according to an alternate embodiment of the present disclosure, for use with cannula assembly 200 and with either seal assembly 100, 200, is generally designated as 520.

Ball seal 520 may have a substantially spherical profile and defines a bore 521 therein. Bore 521 defines a central longitudinal axis "X" and includes a first aperture 522. Bore 521 terminates at an end wall 523 defining a second aperture 524 therein. First aperture 522 has a diameter "D1" which is relatively larger than a diameter "D2" of second aperture 524. First aperture 522 and second aperture 524 may share a common central axis co-incident with the central longitudinal "X" axis.

Ball seal 520 is configured and dimensioned such that a maximum thickness "D3" of ball seal 520, which defines the dimensions of bore 521, is relatively larger than a thickness "D4" of end wall 523. It is contemplated that diameter "D1" of bore 521 is selected so as to receive cylindrical wall 134 of seal cover 130 (see FIGS. 3-5) when ball seal 520 is in a first orientation, or to receive cylindrical inner wall portion 312b of seal holder 310 (see FIGS. 6-8) when ball seal 520 is in a second orientation. It is further contemplated that diameter "D2" of end wall 523 is selected to define an instrument seal.

Ball seal 520 may be fabricated from a suitable resilient and/or elastomeric material, such as, for example, natural rubber, polyisoprene.

While the invention has been particularly shown, and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. A surgical seal assembly for use with a surgical access device, the seal assembly comprising:
    a seal holder including a cylindrical wall portion having a tapered distal portion, the cylindrical wall portion defining a central passage dimensioned to permit passage of a surgical instrument through the seal holder;
    a ball seal supported in the central passage of the seal holder, the ball seal including a distal aperture and a proximal aperture, wherein one of the distal and proximal aperture is dimensioned for substantial sealed reception of the surgical instrument upon insertion of the surgical instrument into the access device, wherein the ball seal has an outer surface dimensioned for substantial sealing with a first surface of the seal holder upon insertion and a second surface of the seal holder upon withdrawal of the surgical instrument to/from the access device, wherein the ball seal is adapted for angular movement relative to a central longitudinal axis of the seal holder upon angulation of the surgical instrument, and wherein the ball seal longitudinally translates upon the longitudinal displacement of the surgical instrument upon insertion and withdrawal of the surgical instrument to/from the access device, whereby the ball seal substantially maintains the seal with the surgical instrument; and
    a seal cover defining an aperture formed in a transverse wall thereof and is configured for connection with the seal holder for maintaining the ball seal within the central passage of the seal holder, wherein the proximal aperture of the ball seal is in registration with the aperture of the seal cover.

2. The surgical seal assembly according to claim 1, wherein the ball seal is fabricated from at least one of a substantially elastomeric and substantially resilient material.

3. The surgical seal assembly according to claim 1, wherein the ball seal creates a seal against a surface of the seal holder during passage of the surgical instrument through the seal holder in a first direction, and the ball seal creates a seal against a surface of the seal cover during passage of the surgical instrument through the seal holder in a second direction.

4. The surgical seal assembly according to claim 3, wherein the proximal aperture of the ball seal is larger than the distal aperture of the ball seal.

5. The surgical seal assembly according to claim 3, wherein the seal cover includes a cylindrical wall extending from the transverse wall and being configured for positioning in the proximal aperture of the ball seal.

6. The surgical seal assembly according to claim 5, wherein the seal cover includes a sloped portion between the transverse wall and the cylindrical wall.

7. The surgical seal assembly according to claim 3, wherein the distal aperture of the ball seal is larger than the proximal aperture of the ball seal.

8. The surgical seal assembly according to claim 7, wherein the seal holder includes a cylindrical inner wall portion extending proximally from a distal edge of the tapered portion and being configured for positioning in the distal aperture of the ball seal.

9. The surgical seal assembly according to claim 3, wherein the ball seal is substantially spherical.

10. A surgical access device, comprising:
a cannula assembly including a sleeve defining a lumen and supporting a closure valve at a proximal end thereof; and
a seal assembly supported at a proximal end of the cannula assembly, the seal assembly including:
a seal holder including a cylindrical wall portion having a tapered distal portion, the cylindrical wall portion defining a central passage dimensioned to permit passage of a surgical instrument through the seal holder and into the lumen of the cannula assembly;
a ball seal supported in the central passage of the seal holder, the ball seal including a distal aperture and a proximal aperture, wherein one of the distal and proximal aperture is dimensioned for substantial sealed reception of the surgical instrument upon insertion of the surgical instrument into the access device, wherein the ball seal has an outer surface dimensioned for substantial sealing with a surface of the seal holder upon insertion and withdrawal of the surgical instrument to/from the access device, wherein the ball seal is adapted for angular movement relative to a central longitudinal axis of the seal holder upon angulation of the surgical instrument, and wherein the ball seal longitudinally translates upon the longitudinal displacement of the surgical instrument upon insertion and withdrawal of the surgical instrument to/from the access device, whereby the ball seal substantially maintains the seal with the surgical instrument; and
a seal cover defining an aperture formed in a transverse wall thereof and is configured for connection with the seal holder for maintaining the ball seal within the central passage of the seal holder, wherein the proximal aperture of the ball seal is in registration with the aperture of the seal cover.

11. The surgical access device according to claim 10, wherein the ball seal is fabricated from at least one of a substantially elastomeric and substantially resilient material.

12. The surgical access device according to claim 10, wherein the ball seal creates a seal against a surface of the seal holder during passage of the surgical instrument through the seal holder in a first direction, and the ball seal creates a seal against a surface of the seal cover during passage of the surgical instrument through the seal holder in a second direction.

13. The surgical access device according to claim 12, wherein the proximal aperture of the ball seal is larger than the distal aperture of the ball seal.

14. The surgical access device according to claim 12, wherein the seal cover includes a cylindrical wall extending from the transverse wall and being configured for positioning in the proximal aperture of the ball seal.

15. The surgical access device according to claim 14, wherein the seal cover includes a sloped portion between the transverse wall and the cylindrical wall.

16. The surgical access device according to claim 12, wherein the distal aperture of the ball seal is larger than the proximal aperture of the ball seal.

17. The surgical access device according to claim 16, wherein the seal holder includes a cylindrical inner wall portion extending proximally from a distal edge of the tapered portion and being configured for positioning in the distal aperture of the ball seal.

18. The surgical access device according to claim 12, wherein the ball seal is substantially spherical.

19. The surgical access device according to claim 10, wherein the cannula assembly includes a cannula housing supported on a proximal end of the sleeve, wherein the cannula housing is configured to support the closure valve therein and is configured to selectively engage the seal assembly.

20. The surgical access device according to claim 19, wherein the cannula housing includes a port opening formed therein and is configured for operative receipt of a luer fitting therein.

21. The surgical access device according to claim 1, wherein the cylindrical wall of the seal holder extends into the ball seal.

22. The surgical access device according to claim 1, wherein at least two annular seals are defined upon at least one of insertion and withdrawal of the surgical instrument to/from the access device.

23. The surgical access device according to claim 10, wherein at least two annular seals are defined upon at least one of insertion and withdrawal of the surgical instrument to/from the access device.

* * * * *